United States Patent [19]

Schmidt

[11] Patent Number: 4,603,143
[45] Date of Patent: Jul. 29, 1986

[54] FREE-FLOWING, HIGH DENSITY, FAT SOLUBLE VITAMIN POWDERS WITH IMPROVED STABILITY

[75] Inventor: Douglass N. Schmidt, Grosse Ile, Mich.

[73] Assignee: BASF Corporation, Wyandotte, Mich.

[21] Appl. No.: 648,909

[22] Filed: Sep. 7, 1984

Related U.S. Application Data

[63] Continuation-in-part of Ser. No. 490,976, May 2, 1983, abandoned.

[51] Int. Cl.$^4$ ............................................. A61K 31/355
[52] U.S. Cl. ..................................................... 514/458
[58] Field of Search ................. 424/284, 236; 514/458

[56] References Cited

U.S. PATENT DOCUMENTS

| | | | |
|---|---|---|---|
| 2,858,215 | 10/1958 | Espoy | 424/356 |
| 3,247,064 | 4/1966 | Maekawa et al. | 424/34 |
| 3,421,282 | 1/1969 | Hasegawa et al. | 424/33 |
| 3,608,083 | 9/1971 | Bunnell et al. | 424/284 |
| 3,914,430 | 10/1975 | Cannalonga et al. | 424/284 |
| 3,947,596 | 3/1976 | Cannalonga et al. | 424/344 |

FOREIGN PATENT DOCUMENTS

| | | |
|---|---|---|
| 62225 | 10/1982 | European Pat. Off. |
| 52-66615 | 11/1977 | Japan |
| 53-15429 | 2/1978 | Japan |

OTHER PUBLICATIONS

Chem. Abst. 87 172906(n) (1977)–Sawai et al.
Chem. Abst. 90 21061(u) (1979)–Chumachenko et al.
Chem. Abst. 98 196703(x) (1983)–Schumacher et al.
Chem. Abst. 98 105,968(y) (1983)–Polasek et al.

*Primary Examiner*—Douglas W. Robinson
*Attorney, Agent, or Firm*—David L. Hedden; Joseph D. Michaels

[57] ABSTRACT

Vitamin-active powders which are more free-flowing and stable, than conventional fat-soluble vitamin powders are prepared utilizing special silicon-containing materials which are predominately in the form of substantially discrete agglomerates. The agglomerates are such that preferably 50 percent of the total have a minimum length, width, or both of 300 microns.

2 Claims, 3 Drawing Figures

FREE-FLOWING, HIGH DENSITY, FAT SOLUBLE VITAMIN POWDERS WITH IMPROVED STABILITY

CROSS REFERENCE TO RELATED APPLICATION

This application is a continuation-in-part of U.S. application Ser. No. 490,976 filed May 2, 1983 now abandoned.

BACKGROUND OF THE INVENTION

1. Field of the Invention

This invention relates to fat-soluble vitamin active powders prepared by the adsorption of certain vitamins on the surface of specified silicon-containing materials.

2. Description of the Prior Art

Heretofore, vitamin E and other oily medicaments have been prepared in powder form by the adsorption of the oily vitamin product onto the surface of such porous fine powders as silicic acid, silicic anhydride and calcium silicate as disclosed in U.S. Pat. Nos. 3,247,064 and 2,858,215. These products tend to be extremely dusty and difficult to handle, and their densities are much lower than 0.5 grams per cubic centimeter. The agglomerated forms of the powders suffer a loss in free-flowing characteristics as a result of such agglomeration.

Such prior art fat-soluble vitamin powders also have been prepared utilizing various processes including spray-drying a vitamin slurry or emulsion containing hydrolyzed gelatin while introducing ultra-fine particle size absorbents into the spray-drying chamber such as disclosed in U.S. Pat. Nos. 3,947,596 and 3,924,430.

SUMMARY OF THE INVENTION

This invention relates to a free-flowing, fat-soluble vitamin-containing powder which has improved stability comprising:
 (a) at least one fat-soluble vitamin material, and
 (b) a silicon containing material predominately in the form of substantially discrete agglomerates.

Generally the discrete agglomerates are such that at least 50 percent of the total number will have a minimum length, width, or both of 300 microns. The use of the described silicon-containing material is essential to obtaining a free-flowing, fat-soluble vitamin containing powder having improved stability.

DRAWINGS

Figure 1:
FIG. 1 is a photomicrograph of ZEOSYL 110 silicon dioxide at a magnification of 25 times. The scale is approximately 1.0 centimeter=400 microns.
Figure 2:
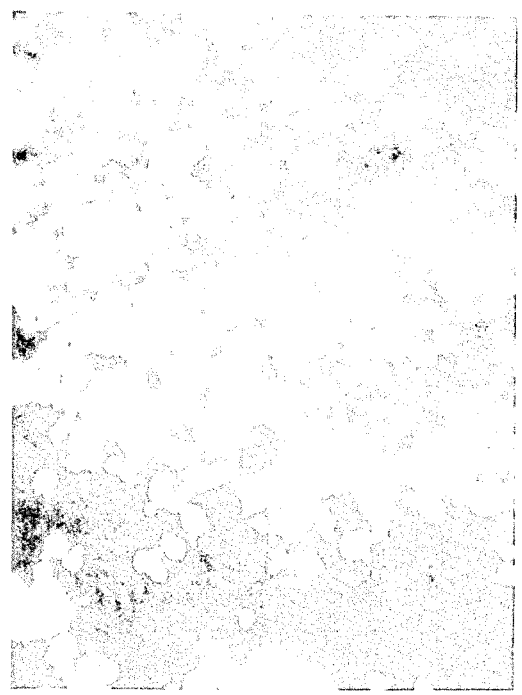
FIG. 2 is a photomicrograph of SIPERNAT 22 silicon dioxide at a magnification of 25 times. The scale is approximately 1.0 centimeter=400 microns.

All three of these photomicrographs show agglomerates of silicon dioxide primary particles. However, the agglomerates of primary particles shown in FIG. 1 and FIG. 2 are amorphous and appear to be fused together. On the other hand, the agglomerates of primary particles in FIG. 3 are substantially discrete and are in the form of large three dimensional secondary particles having a length, width, or both of 300 microns in most cases.

DETAILED DESCRIPTION OF THE INVENTION

Figure 3:
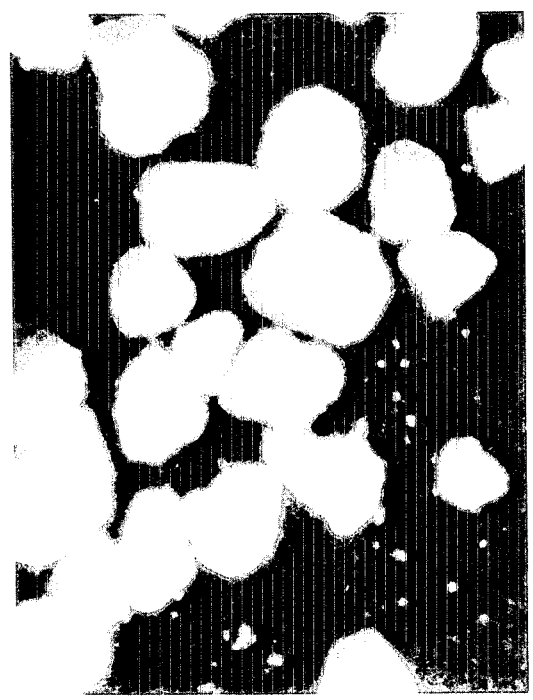
FIG. 3 is a photomicrograph of HI-SIL 213 silicon dioxide at a magnification of 25 times. The scale is approximately 1.0 centimeter=400 microns.

Free-flowing, fat-soluble vitamin powders suitable for direct compression into tablets can be prepared by mixing said vitamins in the form of liquids together with a silicon-containing adsorbent material whose predominant form, as shown in FIG. 3 is that of substantially discrete agglomerates. The size of these agglomerates is such that preferably at least 50 percent of the total number of agglomerates will have a minimum length, width, or both of 300 microns. For purposes of this invention disclosure, any agglomerate which has a particle size of less than 50 microns is not counted in the total when determining whether 50 percent of the total number of agglomerates has a minimum length, width, or both of 300 microns. Furthermore, silicon-containing adsorbent material is considered to be in the form a substantially discrete agglomerates if one skilled in the art considers a photomicrograph of it at a magnification of 25 times to more closely resemble FIG. 3 rather than FIG. 1 or FIG. 2. The fat-soluble vitamins are metered into the adsorbent powder materials which are maintained under constant agitation so as to allow the liquids to become adsorbed on the surfaces of the powder. The fat-soluble vitamin can be mixed with various stabilizing agents known to those skilled in the art to maintain the potency of the vitamin over reasonable periods of storage. The fat-soluble vitamin in liquid form can be reduced in viscosity before mixing, if necessary, by the application of a moderate amount of heat. This speeds the process of adsorption upon the addition of the vitamin to the adsorbent powder.

In the process of the invention, no water, diluents, emulsifiers or other adjuvents need be added to the vitamin which is utilized in the liquid form in the process of the invention. Thus, the various processes of the prior art which involve the use of water and emulsifiers, such as gelatin and starch, and spray-drying techniques are unnecessary to the process of the invention. It has been observed that the mixing process of the invention results in some release of heat as the liquid vitamin is adsorbed on the surface of the adsorbent powder. This is advantageous in that the adsorption of the liquid vitamin is increased as the temperature of the mixture increases.

While this invention includes products and processes prepared utilizing various fat-soluble vitamins, the preferred embodiment of this invention is a free-flowing, substantially non-agglomerated at the secondary particle size level, high density vitamin E powder suitable for direct compression tableting techniques.

Vitamin E comprises a group of natural substances known as tocopherols. These fat-soluble, closely related chemical compounds are found in vegetable oils such as wheat germ oil, rice oil, soybean oil and the like. The greatest biological activity of the tocopherols is found in the alpha-tocopherol while the isomers beta-, gamma-, delta-, epsilon-, zeta- and eta-tocopherols having vitamin E activity to a lesser extent. The tocopherols and their esters such as tocopherol acetate, tocopherol palmitate, tocopherol succinnate and the like are normally water-insoluble and oily, waxy or low-melting products which make them unsuitable for certain pharmaceutical applications, particularly those in which a powder is required such as in vitamin tablets and capsules.

Any of the tocopherols, their esters or compounds convertible to either tocopherols or their esters are suitable for use in the process of this invention. In order to insure the desired stability of activity of the vitamin E in the final powder form, it is preferred to use tocopherol esters in the process of this invention. The preferred ester for use in accordance with this invention is dl-alpha-tocopherol acetate (vitamin E acetate). In the preparation of the powders of the invention, sufficient tocopherol acetate or other fat-soluble vitamin is used to insure that the resulting powders contain from about 40 to 60 percent by weight activity. The amount of vitamin activity expressed as present in the powder is that which would be present if the vitamin activity is present as the pure vitamin.

The process of the invention is also applicable to the other fat-soluble vitamins which are generally considered to be vitamins A, D and K. The products and processes of the invention contemplate the use of at least one fat-soluble vitamin in the preparation of said vitamin powders. In addition, it is contemplated that mixtures of vitamins or other nutrient materials which are soluble or dispersible in the fat-soluble vitamins can be utilized in the process of the invention to prepare free-flowing, substantially non-agglomerated, vitamin-active, powdered products.

Of critical importance in the process disclosed and claimed herein is the use of silicon-containing particulate materials with the properties previously set forth. These materials must be capable of an appreciable capacity to adsorb water or oil, and preferably have an oil adsorption capacity of about 150 to about 400 pounds per 100 pounds. Suitable adsorbent materials include silicic acid, silicas, alkali metal silicates and the like which have the properties set forth previously.

A characteristic of the products of the invention which distinguishes these products from those of the prior art is the fact that they are free-flowing, fat-soluble vitamin powders having improved stability. These properties evidently result from the use of the specific silicon-containing particulate materials.

The density of the vitamin products of the invention is greater than 0.5 grams per cubic centimeter which is substantially greater than products of the prior art prepared, for instance, utilizing spray drying processes. Since no water is added during the preparation of such powders, the moisture content of the powders is influenced mainly by the amount of moisture absorbed from the air during preparation of the powders.

The following examples illustrate the various aspects of the invention but are not intended to limit its scope. Where not otherwise specified throughout this specification and claims, temperatures are given in degrees centigrade and parts, percentages and proportions are by weight.

The physical properties of the silicon dioxides used in the following Examples and shown in FIGS. 1, 2, and 3 are as follows:

TABLE I

| Physical Properties of Commercial Silicon Dioxide Powders | | | |
|---|---|---|---|
| | HI-SIL 213 | SIPERNAT 22 | ZEOSYL 110SD |
| Bulk Density (grams/cc) | 0.260 | 0.220 | 0.168 |
| Flowability | >250 | no flow | no flow |
| Particle Size Distribution (% weight retained) | | | |
| 20 mesh sieve | 0 | 0 | — |
| 40 mesh sieve | 19 | 0 | 2.0 |
| 60 mesh sieve | 39.2 | 2 | 1.92 |
| 80 mesh sieve | 20.6 | 19 | 13.48 |
| 100 mesh sieve | 8.8 | 14 | 66.68 |

EXAMPLE 1

This example illustrates the procedure for the preparation of a free-flowing, high density, vitamin E acetate powder suitable for direct compression in the formation of tablets.

Utilizing a three kilogram capacity laboratory V-blender (Patterson-Kelley) equipped with an oil addition funnel and a powder intensifier bar, sufficient hydrated silicon dioxide (1000 grams) sold under the trademark "HI-SIL 213" by PPG Industries, and shown in FIG. 3, was added to make a two kilogram batch of finished vitamin E powder. A feed grade vitamin E acetate in the amount of 1050 grams was warmed to a temperature of 60° C. and then introduced slowly (over a period of 20 minutes) through an addition funnel connected to the intensifier bar of the blender. The blender was operated at 20 rpm with the intensifier bar operating at 1000 rpm, while the addition was taking place.

After enough vitamin E acetate was added to produce vitamin E powder with a 1 to 2 percent by weight overage in potency beyond 50 percent by weight, the resultant adsorbate was allowed to mix for another 20 minutes under the same blender conditions. The warm vitamin E powder was discharged from the blender and collected. After cooling the powder to room temperature, the bulk density and particle size was determined by adding 1000 ml of the vitamin E powder to a 1 liter graduated cylinder. The cylinder and vitamin E powder were weighed to the nearest 0.1 gram, and then the cylinder was tapped 12 times on the bench top and the resultant volume recorded to the nearest milliliter. The bulk density in pounds per cubic foot was calculated from these measurements.

The particle size distribution was evaluated utilizing a CSC Scientific Sieve Shaker utilizing a 10 gram sample and a No. 5 setting for a period of 15 minutes.

The finished vitamin E powder had a bulk density of 0.503 grams per cubic centimeter before tapping in the manner described above and 0.559 grams per cubic centimeter after tapping. The sieve analysis of this product was as follows:

Percent by weight retained upon the 20 mesh sieve=2.6 percent by weight.

Percent retained on 40 mesh sieve=6.9 percent by weight.

Percent retained on 60 mesh sieve=18.3 percent by weight.

Percent retained on 80 mesh sieve=14.6 percent by weight.

Percent retained on 100 mesh sieve=9.1 percent by weight.

Percent passing through 100 mesh sieve=48.5 percent by weight.

The flowability of the vitamin E powder was evaluated utilizing a test procedure described as follows: A device sold under the trademark FLODEX was used to test flowability. In this method, a 50 gram sample is added to a cylinder assembly having a calibrated opening at the bottom thereof. The flow index is the reciprocal times 1000 of the diameter of the smallest orifice through which the powder will flow. The flowability was found to be 250 which is the highest possible flodex flowability rating.

EXAMPLE 2

(Comparative example—forming no part of this invention)

Example 1 was repeated utilizing a silicon dioxide sold under the trademark ZEOSYL 110 by the J. M. Huber Corporation and is shown in FIG. 1.

The bulk density was found to be 0.389 grams per cubic centimeter before tapping and 0.422 grams per cubic centimeter after tapping. The particle size, as indicated by the proportion of particles retained on standard sieves ranging from 20 mesh through 100 mesh, was evaluated on a Cenco-Meinzer sieve shaker with a setting of 7 for a period of 10 minutes using a 25 gram sample size. Results were as follows:

Percent by weight retained on the 40 mesh sieve=2.0.

Percent by weight retained on the 60 mesh sieve=1.9.

Percent by weight retained on the 80 mesh sieve=13.5.

Percent by weight retained on the 100 mesh sieve=15.9.

Percent by weight passing through 100 mesh sieve=66.7.

The flowability index as determined by the above procedure was less than 50 (essentially no flow).

In addition to measuring the physical properties of the powder prepared in Example 1, the stability of the Vitamin E acetate in the powder against hydrolysis to free tocopherol, which is quite unstable, was also determined. This was determined by mixing 49.9 percent $CaCO_3$, 45 percent MgO, 4.9 percent trace minerals (including copper containing minerals) and 0.2 of the Vitamin E acetate adsorbate, and allowing the mixture to set at room temperature under these alkaline conditions.

Table II which follows summarizes the results of this experiment. It will be noted from Table II that three experiments were run using different silicon dioxides to make the Vitamin E adsorbates. The particular silicon dioxide used is shown in the Table.

TABLE II

| Silicon Dioxide Used to Prepare the Vitamin E Adsorbate | Percentage of Vitamin E Remaining After the Designated Times | | | | |
|---|---|---|---|---|---|
| | Initially | 2 weeks | 4 weeks | 6 weeks | 8 weeks |
| HI-SIL 213 | 100 | 83.1 | 84.6 | 77.8 | 72.1 |
| SIPERNAT 22 | 100 | 78.7 | 64.5 | 55 | 48.5 |
| ZEOSYL 110 | 100 | 55.8 | 36.2 | 28.5 | 22.6 |

Table II indicates that Vitamin E powders prepared with the silicon-containing material within the scope of this invention are more stable against hydrolysis to tocopherol than those prepared with silicon-containing materials outside the scope of this invention.

It is also believed that Vitamin E powders prepared with the silicon-containing materials within the scope of this invention have improved bioavailability.

While this invention has been described with reference to certain specific embodiments, it will be recognized by those skilled in the art that many variations are possible without departing from the scope and spirit of the invention, and it will be understood that it is intended to cover all changes and modifications of the invention disclosed herein for the purposes of illustration which do not constitute departures from the spirit and scope of the invention.

The embodiments of the invention in which an exclusive property or privilege is claimed are defined as follows:

1. A stable, free-flowing Vitamin E or Vitamin E acetate-containing powder comprising:
   (a) Vitamin E or Vitamin E acetate in an amount sufficient to yield a content of about 40 to about 60 percent by weight based upon the total weight of the powder, and
   (b) a silicon containing adsorbent in the form of substantially discrete nonamorphous agglomerates, at least 50 percent of said agglomerates having a minimum length, width or both of 300 microns.

2. A process for making a dry, finely divided, free-flowing vitamin E or Vitamin E acetate-containing powder comprising:
   (a) adding a silicon-containing adsorbent in the form of substantially discrete nonamorphous agglomerates, at least 50 percent of said agglomerates having a minimum length, width, or both of 300 microns, to a container, and, thereafter,
   (b) adding thereto while mixing, a liquid form of a Vitamin E or Vitamin E acetate in an amount sufficient to yield a content of about 40 to about 60 percent by weight based upon the total weight of the powder.

* * * * *